US009977860B2

(12) United States Patent
Cheng (10) Patent No.: US 9,977,860 B2
(45) Date of Patent: May 22, 2018

(54) DIFFERENTIAL DISSOCIATION AND MELTING CURVE PEAK DETECTION

(71) Applicant: APPLIED BIOSYSTEMS, LLC, Carlsbad, CA (US)

(72) Inventor: Francis T. Cheng, Palo Alto, CA (US)

(73) Assignee: Applied Biosystems, LLC, Carlsbad, CA (US)

( * ) Notice: Subject to any disclaimer, the term of this patent is extended or adjusted under 35 U.S.C. 154(b) by 170 days.

(21) Appl. No.: 14/259,057

(22) Filed: Apr. 22, 2014

(65) Prior Publication Data

US 2014/0343862 A1   Nov. 20, 2014

Related U.S. Application Data

(63) Continuation of application No. 12/020,369, filed on Jan. 25, 2008.

(60) Provisional application No. 61/023,674, filed on Jan. 25, 2008, provisional application No. 60/898,310, filed on Jan. 30, 2007.

(51) Int. Cl.
*G06F 19/10* (2011.01)
*C12Q 1/68* (2018.01)

(52) U.S. Cl.
CPC .......... *G06F 19/10* (2013.01); *C12Q 1/6844* (2013.01)

(58) Field of Classification Search
None
See application file for complete search history.

(56) References Cited

U.S. PATENT DOCUMENTS

| 4,175,258 A | 11/1979 | Borkowski et al. |
| 5,323,337 A | 6/1994 | Wilson et al. |

OTHER PUBLICATIONS

The Mathworks, Inc. Curve Fitting Toolbox for Use with MATLAB®. Software Documentation. Oct. 2004. Excerpt of pp. 2-25-2-31, 3-69 and 3-70.*
Barclay, V.J. et al., "I.P Application of Wavelet transforms to experimental spectra: Smoothing, denoising, and data set compression", *Analytical Chemistry*, 1997, 69, 78-90.
Gabarro, J., "Numerical Analysis of Thermal Denaturation of Nucleic Acids", *Analytical Biochemistry*, vol. 91, 1978, 309-322.
Gorry, P.A., "General least—squares smoothing and differentiation of nonuniformly spaced data by the convolution method", *Analytical Chemistry*, 1991, 63, 534-536.

(Continued)

*Primary Examiner* — Soren Harward
(74) *Attorney, Agent, or Firm* — Mauriel Kapouytian Woods LLP; Lana Akopyan; Michael Mauriel (57) ABSTRACT

Systems and methods are provided for processing a melting or dissociation curve of a DNA or other sample, for example, during PCR processing. In some embodiments, detection of the melting point and melting curve behavior can be enhanced by taking a derivative of the curve, and detecting peaks in the differential dissociation curve. In some embodiments, the derivative operation can comprise the use of edge-processing, or other detection algorithms. In some embodiments, the dissociation analysis can comprise removing low-frequency (or pedestal) components of the differential dissociation curve. In some embodiments, the differential dissociation curve can exhibit a smoothed or more regular appearance than the raw detected data.

17 Claims, 9 Drawing Sheets

(56) References Cited

OTHER PUBLICATIONS

Kim, J.S. et al., "Solid State Comms", *Temperature dependent emission spectra of M2sio4 Eu2C(M=ca, sr, Ba) phosphors for green and greenish white LED's*, 2005, 133, 445-448.

Sklar, L.A. et al., "The dynamics of ligand-receptor instructions", *real time analyses of association , dissociation and internalization of an n-formyl peptide and its receptors on the human neutrophil*. Journal of Biological Chemistry, 1984, 259, 5661-5669.

Wiersma, D.S. et al., "S.A temperature—tunable random laser", *Nature 414*, 2001, 708-709.

Wittwer, C T. et al., "High resolution genotyping by amplicon melting analysis using LCGreen", *Clinical Chemistry*, vol. 49, No. 6, 2003, 853-860.

\* cited by examiner

DIFFERENTIAL DISSOCIATION AND MELTING CURVE PEAK DETECTION

RELATED APPLICATIONS

This application is a continuation of U.S. application Ser. No. 12/020,369 filed Jan. 25, 2008, which claims priority to U.S. Provisional Patent Application No. 60/898,310 filed Jan. 30, 2007, entitled "Differential Dissociation and Melting Curve Peak Detection," and to U.S. Provisional Patent Application No. 61/023,674 filed Jan. 25, 2008, to Francis T. CHENG et al. entitled "Methods of Dissociation Melt Curve, Analysis and Calibration," both of which are incorporated by reference in their entireties.

BACKGROUND

DNA amplification methods provide a powerful and widely used tool for genomic analysis. Polymerase chain reaction (PCR) methods, for example, permit quantitative analysis to determine DNA copy number, sample source quantitation, and transcription analysis of gene expression. DNA analysis methods allow the detection of single base changes in specific regions of the genome, such as single nucleotide polymorphisms (SNPs), SNP analysis and other techniques facilitate the identification of mutations associated with specific diseases and conditions, such as various cancers, thalassemia, or others.

Many applications of PCR require the accurate generation of desired amplification products versus the production of undesired artifacts. One useful approach for validating the integrity of PCR reactions relies on melting curve analysis to discriminate artifact from real amplification product. Melting curve analysis can also be used to differentiate the various products of multiplexed DNA amplification, and to extend the dynamic range of quantitative PCR. DNA melting curve analysis can also be a powerful tool for optimizing PCR thermal cycling conditions, since the point at which DNA fragments or other material melts and separate can be more accurately pinpointed.

One known approach for DNA melting curve analysis utilizes fluorescence monitoring with intercalating double-strand-DNA specific dyes, such as for example, SYBR Green. The SYBR Green dye attaches to the DNA as double-stranded DNA amplification products are formed, and continues to bind to the DNA as long as the DNA remains double-stranded. When melting temperatures are reached, the denaturation or melting of the double-stranded DNA is indicated and can be observed by a significant reduction in fluorescence, as SYBR Green dissociates from the melted strand. The detected dye fluorescence intensity typically decreases about 1000-fold during the melting process. Plotting fluorescence as a function of temperature as the sample heats through the dissociation temperature produces a DNA melting curve. The shape and position of the DNA melting curve is a function of the DNA sequence, length, and GC/AT content.

Figure 1:
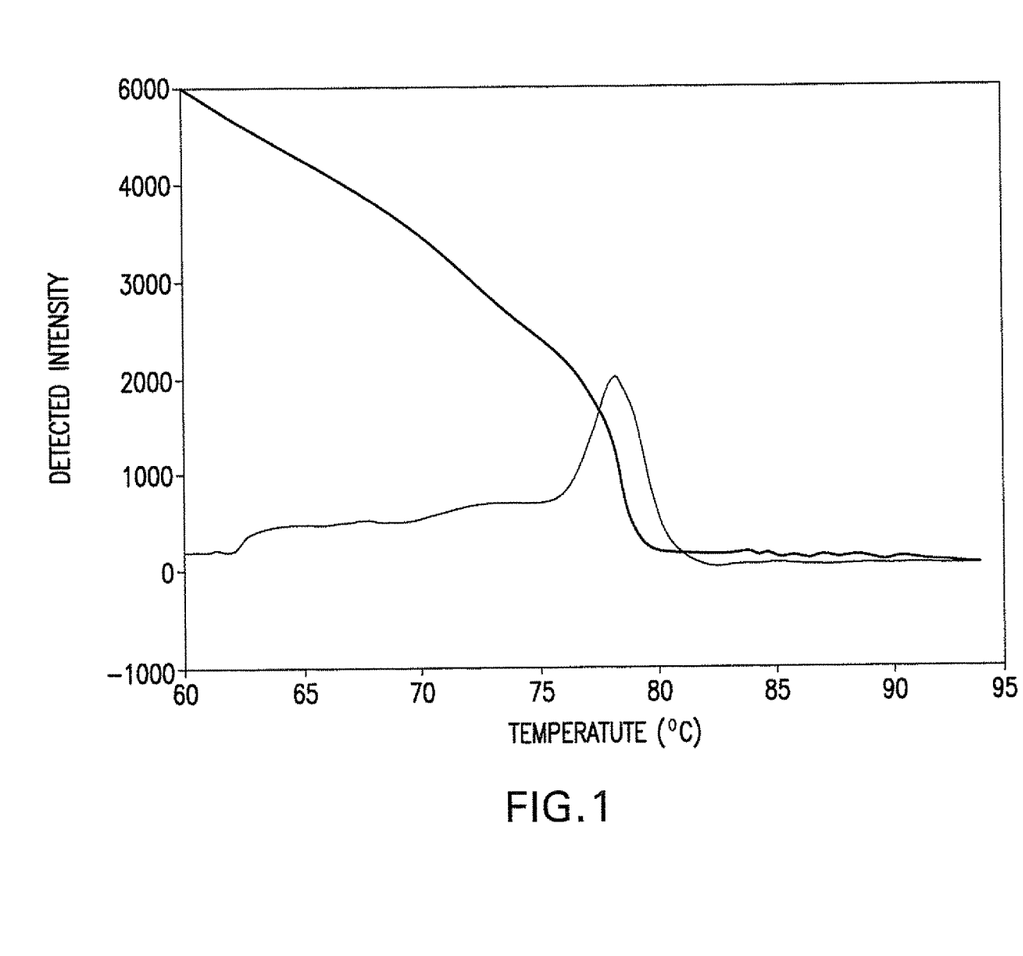
FIG. 1 illustrates a dissociation/melting curve, according to various embodiments of the present teachings.
Figure 2A:
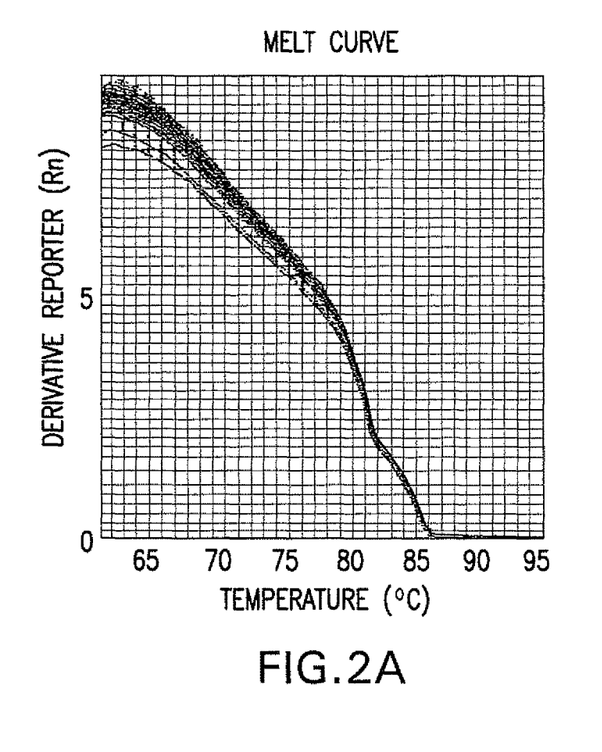
FIGS. 2(A) and 2(B) illustrate a set of melt curves and differential melt curves having multiple products, according to various embodiments of the present teachings.
Figure 2B:
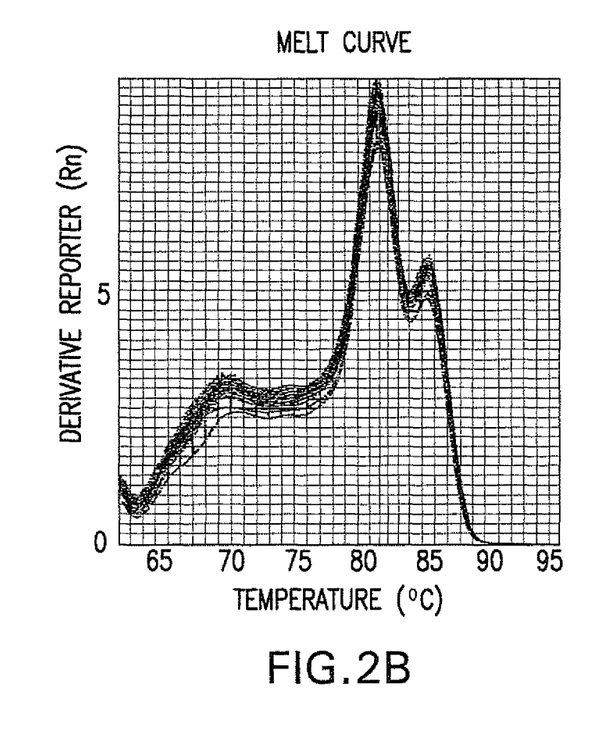

Currently known dissociation/melting curve analysis methods calculate and display the first derivative of multi-component dye intensity data versus temperature, i.e., the differential melting curve. The temperature, $T_m$, at a peak of the differential melting curve characterizes the product of the biochemical reaction. A sample with multiple amplification products will show a melt curve with multiple peaks in the differential melt curve. See generally, for example, FIG. 1 (illustrating a single sample) and FIGS. 2(A) and 2(B) (illustrating multiple samples).

Typically, during melting curve analysis, the raw data fluorescence measurements are taken at uneven or irregular temperature intervals. This can introduce undesired sensitivity to the sampling process along the temperature axis. Conventional signal processing techniques such as filtering, differentiation, and the like, do not apply for data samples at uneven temperature intervals. There is a need for techniques that correct for uneven or irregular temperature interval sampling, and other problems in the field.

For example, calculating the differential dissociation curve can be a noisy process. The melt curve is inherently noisy, due, for example, to sampling or quantization errors, and traditional computational differentiation methods can make noise issues worse. There is a need for techniques that distinguish a genuine signal peak versus a noisy spike, and for techniques that distinguish a sample producing credible melting curve results, versus a sample producing unintelligible data.

Current dissociation curve analysis methods, moreover, typically assume a single peak in a differential dissociation curve. There is a need for melting curve analysis methods for gene expression and other purposes that can detect multiple peaks of a differential melting curve. There is a further need for melting curve techniques that can be applied to, or implemented in, automated validation techniques, among other applications.

SUMMARY

According to various embodiments of the present teachings, systems and methods are provided which receive and analyze fluorescent or other emission data generated by samples in PCR or other processes as temperatures vary during melting or dissociation phenomena. According to various embodiments, the fluorescent emission spectra of one or more DNA or other samples can be captured or received as a function of temperature or other parameters, and the raw dissociation curve plotted. According to various embodiments, the analysis can include interpolating, over sampling, or resampling the source or raw dissociation curve to produce a curve or representation having equally-spaced temperature intervals. According to various embodiments, the analysis can comprise inspecting the spectral plot of the raw dissociation curve to identify curves containing comparatively large amounts of power in upper frequencies, indicating extraneous noise in the detection process. According to various embodiments, dissociation curves whose normalized variance exceeds a predetermined threshold can be discarded as unreliable. According to various embodiments, the analysis can further comprise removing low-frequency components of the raw dissociation curve, to better isolate melting behavior. According to various embodiments, the raw dissociation curve can be subjected to a derivative computation, for example a first derivative, to assist in identifying points of sharpest change in the dissociation data in turn indicating a possible melting point. According to various embodiments, the derivative computation can comprise the application of an edge filter, for example a Canny filter or other filter or computation. According to various embodiments, the dissociation curve after derivative processing can contain multiple identified melting points.

DESCRIPTION

According to various embodiments of the present teachings, systems and methods are provided that operate on raw dissociation data plots to generate a first-order or other derivative plot of the original emission data. According to various embodiments, the emission data can comprise a graph, chart, or other representation of the dye emission of one or more fluorescently-labeled samples, such as DNA samples, as a function of temperature. According to various embodiments, the raw emission data of the dissociation/melting curve or other data can be pre-processed or otherwise conditioned to improve the downstream analysis. According to various embodiments, for example, the analysis can comprise interpolating the measurement data taken at unevenly-spaced temperature intervals into data samples at equally-spaced temperature intervals. According to various embodiments, an equal spacing interpolation, or other resampling or oversampling step, can improve the mathematical integrity or capability of the subsequent calculations, including, for example, to permit Fourier or other frequency-domain transformations. According to various embodiments, the original raw or source data can comprise data samples at irregular temperature intervals, since the rate of change in temperature can vary at different points in the PCR or other cycle or process. According to various embodiments, resampling, oversampling, interpolating, or otherwise processing the fluorescent signal-versus-temperature graph to produce data points at equally-spaced temperature intervals can provide modified data which is capable of being subjected to frequency domain analysis. In some embodiments, raw dissociation data that is interpolated, oversampled, or resampled to produce data points at equally-spaced temperature intervals can be subjected to a Fourier transform, to develop a frequency-domain or spectral representation of the original melting curve, or of processed melting curves derived from the original melting curve. The frequency transform or operator can comprise a discrete-time Fourier transform, a continuous Fourier transform, a Fast Fourier Transform, a wavelet transform, or other transform, algorithm, or operator.

Figure 3:
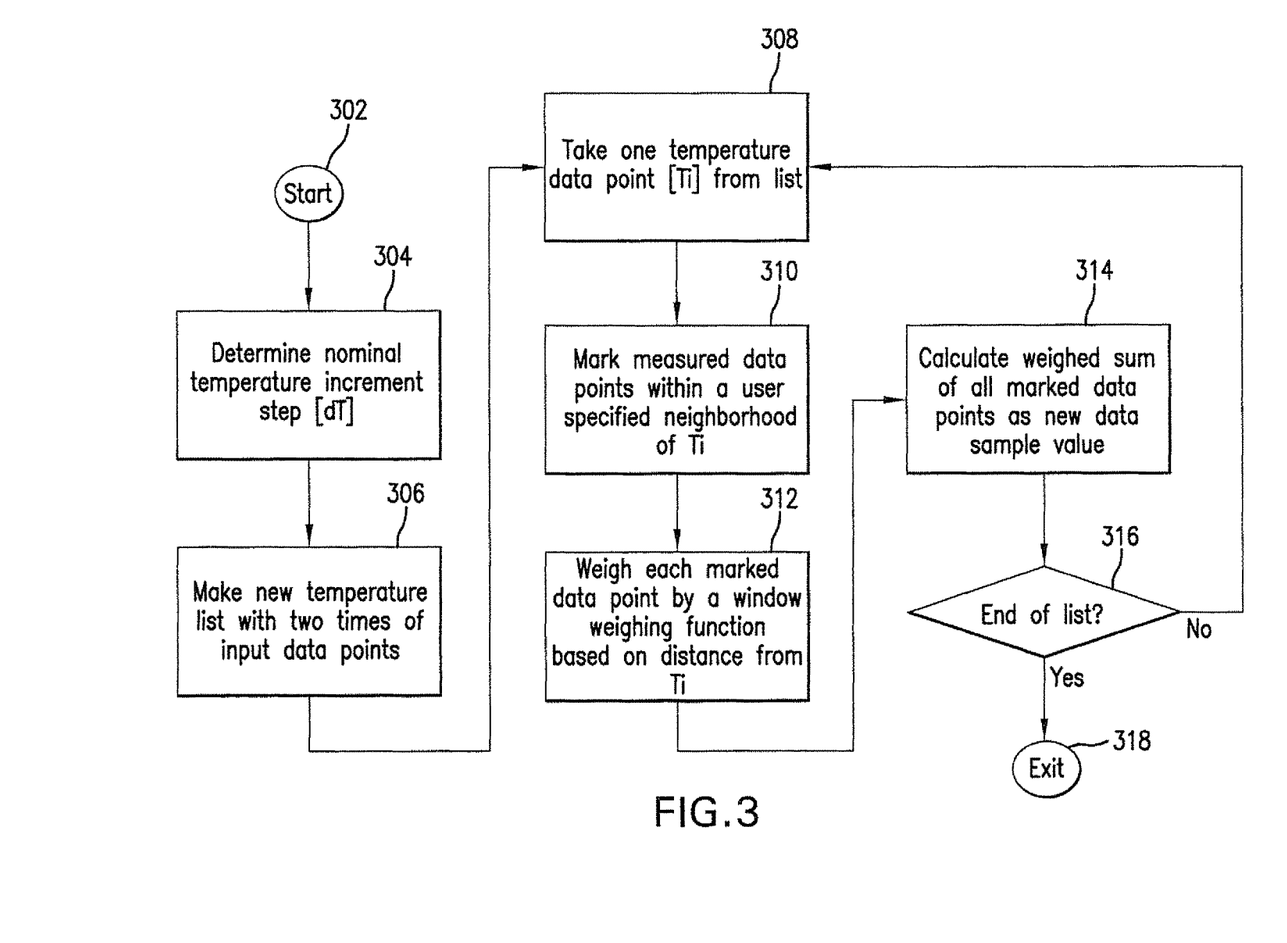
FIG. 3 illustrates a flow diagram of interpolation processing, according to various embodiments of the present teachings.

According to various embodiments, interpolation processing to produce equally-spaced data points along the temperature axis can comprise processing algorithms shown in the flow diagram of FIG. 3. In step 302, processing can begin. In step 304, a nominal temperature increment or step (dT) can be determined, for example, by dividing the total temperature range by the number of data points. In step 306, a new temperature axis or list of temperatures can be generated having double, or another multiple, of the number of original data points. In step 308, one temperature data point (Ti) can be taken from the list. In step 310, the measured data points can be marked with a user-specified or other neighborhood or region of, around, or in proximity to Ti. In step 312, each marked data point can be weighed or adjusted by a window weighting function based on its distance from Ti. In step 314, a weighted sum of all marked data points can be generated or calculated as the new data sample value. In step 316, a determination can be made whether the end of the emission data list has been reached. If the end of the list has been reached, processing can terminate in step 318. If the end of the list has not been reached, processing can return to step 308, repeat, or other action can be taken. According to various embodiments as shown in FIG. 3, the resulting interpolation can produce a data sequence with more data samples than the original data sequence. For example, according to embodiments, the interpolated data sequence can comprise twice the data samples of the original data sequence. In some embodiments, the interpolated data sequence can comprise another integer or non-integer multiple of the original number of samples or data points, or another number of output samples.

According to various embodiments, further processing or data conditioning can be performed on the raw or interpolated dissociation curve or related data. For example, the dissociation analysis can comprise steps that detect and identify noisy data samples, to eliminate the effects of those sources on further analysis. Illustrations of dissociation curves exhibiting different good, marginal, and noisy detected patterns of melt curve behavior are shown, for example, in FIGS. 4(A)-4(C). Noisy data samples can corrupt further PCR or other analysis. The analysis can therefore in one regard reject, remove, or exclude emission data from samples identified as noisy samples from further analysis. According to various embodiments, the noisy data samples can be normalized or otherwise processed for incorporation in further calculations. According to various embodiments, the detection of noisy data samples can comprise applying spectral domain analysis and detection techniques to the raw or interpolated data. According to various embodiments, the dissociation analysis and processing can comprise, for example, calculating a power spectrum of the interpolated melting curve.

Figure 4A:
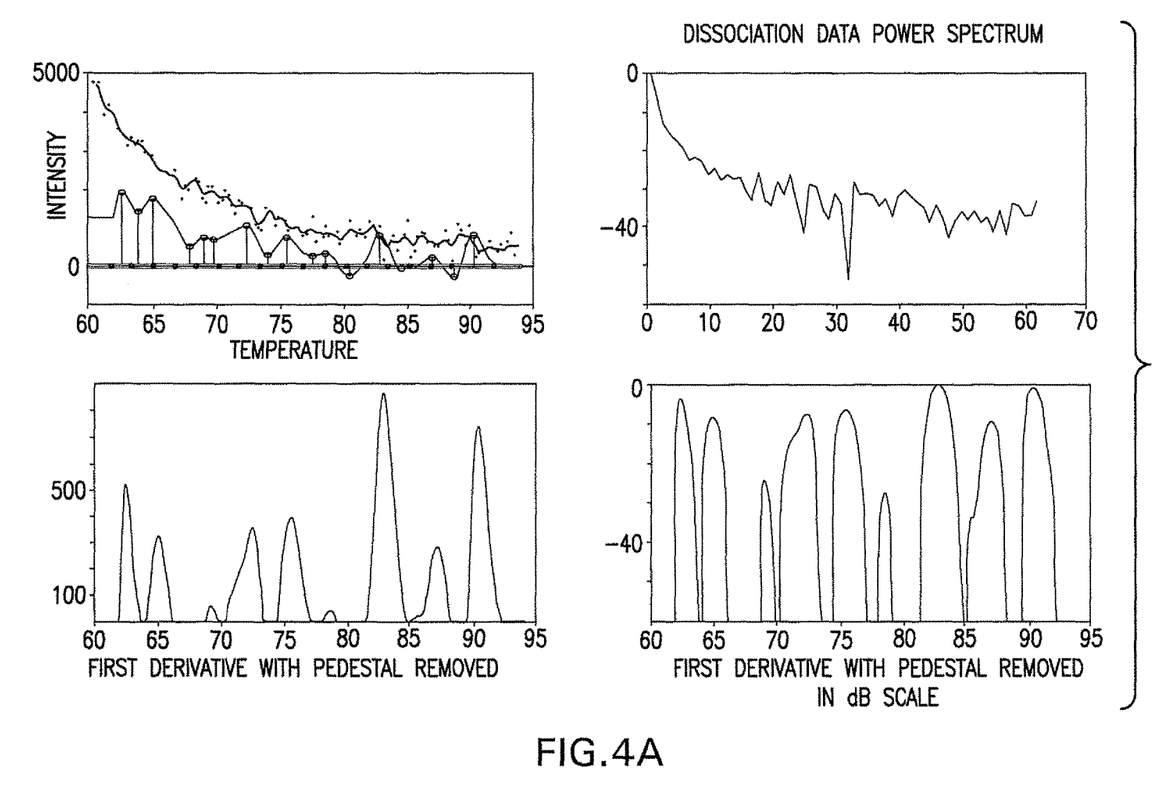
FIG. 4(A) illustrates a melt curve and a set of related derivative and power spectrum curves reflecting noisy sample data, according to various embodiments of the present teachings.
Figure 4B:
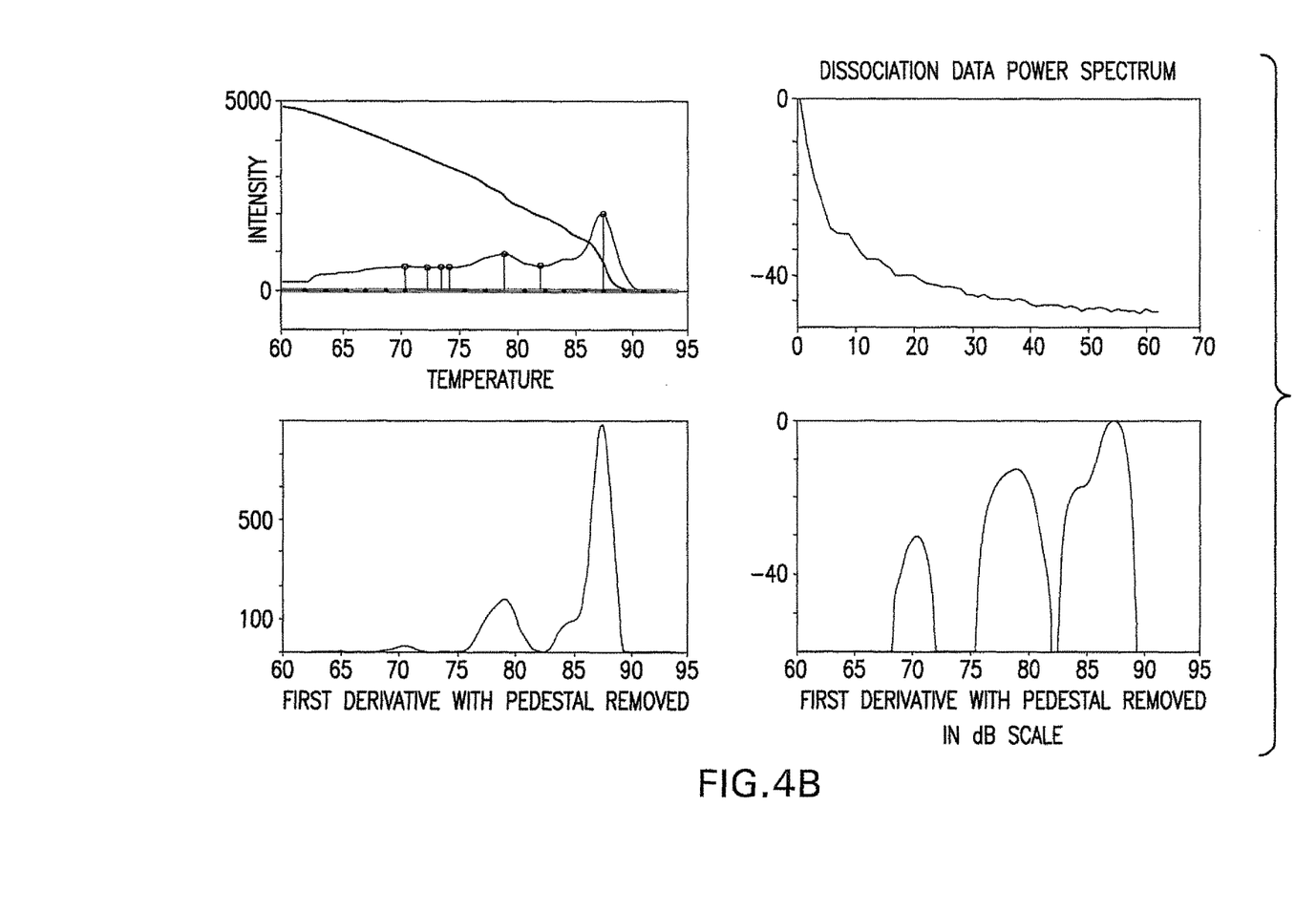
FIG. 4(B) illustrates a melt curve and a set of related derivative and power spectrum curves reflecting good or reliable sample data, according to various embodiments of the present teachings.
Figure 4C:
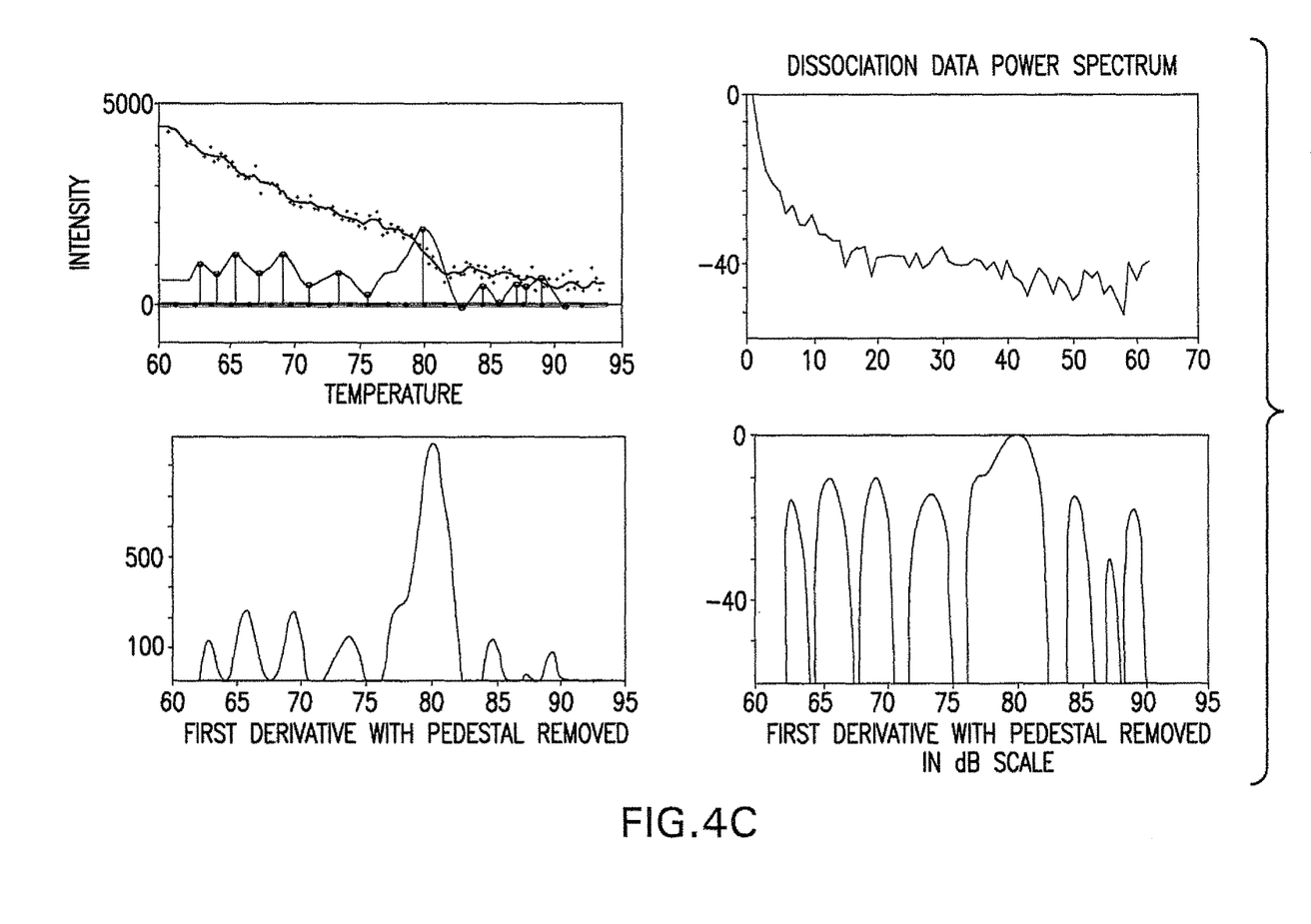
FIG. 4(C) illustrates a melt curve and a set of related derivative and power spectrum curves reflecting marginal sample data, according to various embodiments of the present teachings.

Computed power spectra of a noisy, good, and marginal well or sample are shown in the upper-right graph of FIGS. 4(A), 4(B), and 4(C), respectively. In general, a noisy well or sample will tend to show a significant amount of power present in the upper frequency ranges, indicating the random, spurious, or rapid spikes or transitions associated with noise content. According to various embodiments, the dissociation analysis can, for example, comprise setting the dissociation curve data sampling rate at about 1 Hz, and calculating a normalized variance of the power spectrum of the dissociation curve from about ¼ Hz to about ½ Hz. Other sampling rates can be used.

According to various embodiments, the power spectrum of an interpolated well or sample series can be quantitatively processed to identify noisy wells or samples. For example, a normalized variance of the power spectrum curve of the sample series can be computed. In some embodiments, if the normalized variance of the dissociation curve is above a defined noise discrimination threshold, the sample data can be classified as noise. According to various embodiments, the noise discrimination threshold can comprise a user-defined threshold. According to various embodiments, the noise discrimination threshold can comprise an automatically-generated threshold, for instance based on statistical measures. According to various embodiments, the noise discrimination threshold can comprise an empirically-derived threshold, for instance, an average threshold of known good wells or samples. In some embodiments, the normalized, rather than absolute, variance or other statistical measure can be used to accommodate data from different samples, for example, to process samples displaying different initial fluorescent intensities.

Figure 5A:
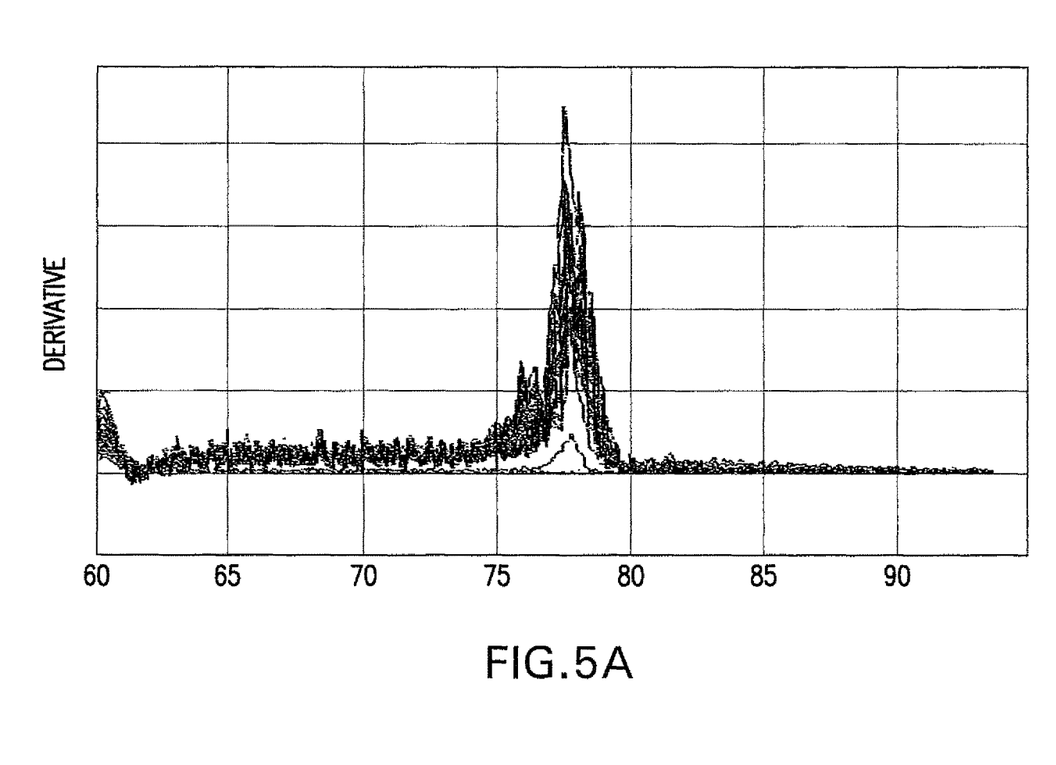
FIG. 5(A) illustrates the generation of a set of differential melt curves, according to various embodiments of the present teachings.
Figure 5B:
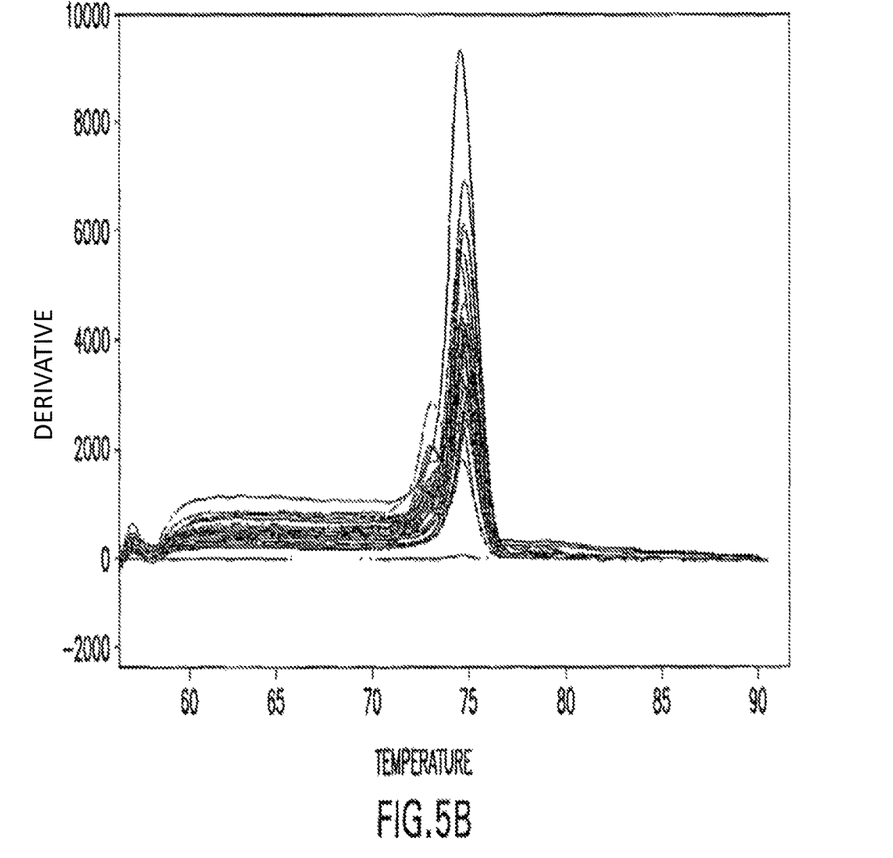
FIG. 5(B) illustrates the generation of a set of differential melt curves, according to various embodiments of the present teachings in another regard.

According to various embodiments, the analysis can comprise filtering the interpolated temperature data by a Gaussian kernel or other function. According to various embodiments, the filtered, interpolated data can be further filtered or processed by the derivative of the Gaussian kernel, or other derivative or other function. According to various embodiments, application of a derivative function, for instance a first-order derivative function, can produce a differential melt or dissociation curve, such as, for example, the curves shown in FIG. 5(A). FIG. 5(A) displays differential traces for a set of multiple samples or wells. According to various embodiments, when a first-order derivative is computed, the analysis can comprise utilizing a Canny edge detection algorithm filtering technique to calculate the first derivative of the dissociation curve. The Canny filtering technique is, for example, described in: J. Canny, "A Computational Approach to Edge Detection", IEEE Transactions on Pattern Analysis and Machine Intelligence, Vol. 8, No. 6, November 1986, which document is herein incorporated in its entirety by reference. As, for example, illustrated in FIG. 5(B), edge detection processing can reduce the effects of sharpened transitions in noisy derivative signals.

According to various embodiments, the dissociation analysis can further comprise extrapolating data points at the beginning and at the end of the raw or interpolated dissociation curve, before the first derivative calculation. This can, for instance, improve the correctness or accuracy of the first derivative calculations at the beginning and at the end of the dissociation curve.

Figure 6:
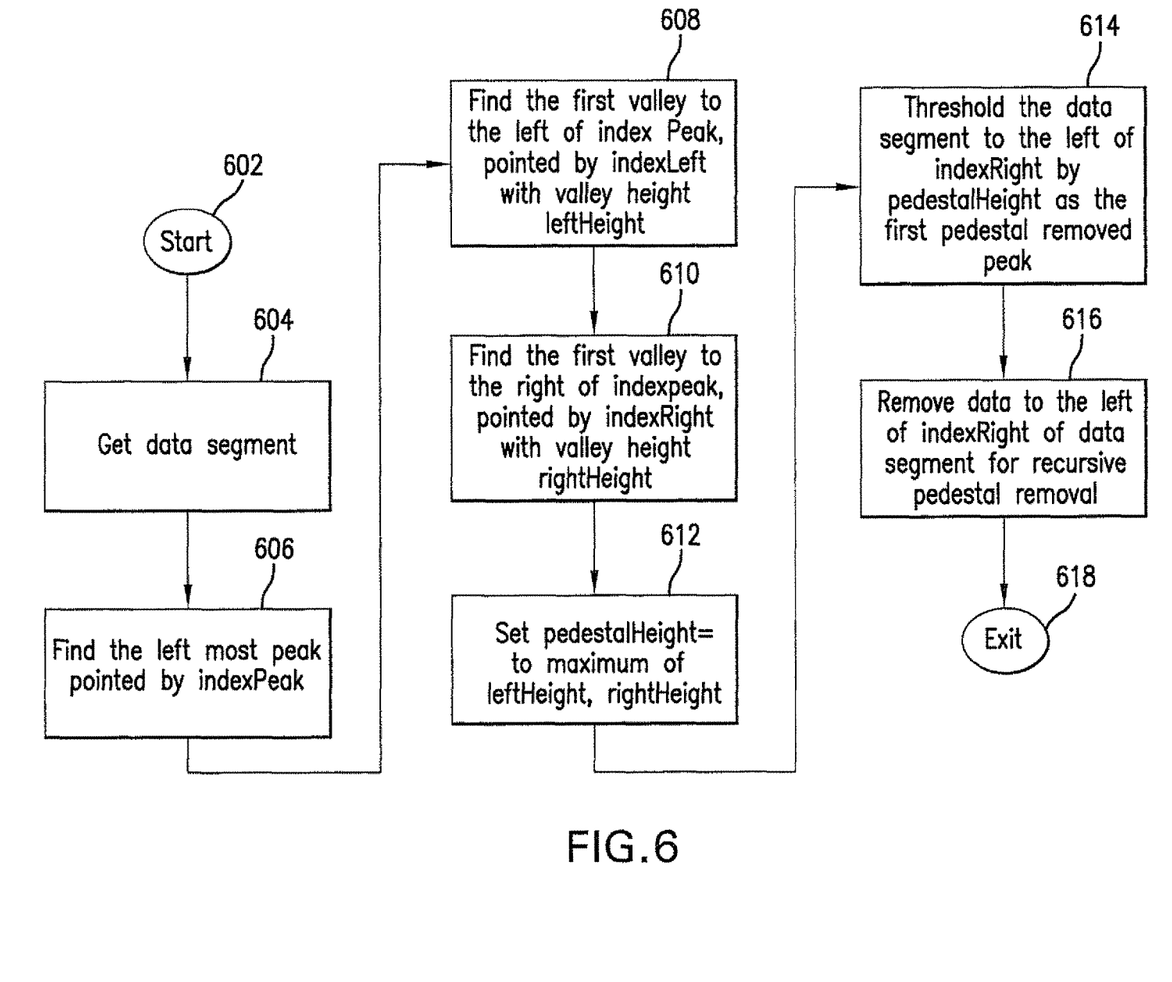
FIG. 6 illustrates a flow diagram of a pedestal removal algorithm, according to various embodiments of the present teachings.

According to various embodiments, the dissociation analysis can comprise detecting and analyzing the peaks of the first derivative of the dissociation curve (i.e., the differential melting curve), that sit on top of a low-frequency "pedestal" or offset. According to various embodiments, the "pedestal" can designate very low frequency components of the differential melting curve. According to various embodiments, the analysis can comprise removing the pedestal or low-frequency components, and evaluating the heights of the modified differential melting curve peaks left after the pedestal or baseline is subtracted or otherwise compensated for. According to various embodiments, techniques for removing the pedestal can comprise the processing shown in the flow diagram illustrated in FIG. 6. In step 602, processing can begin. In step 604, a data segment can be received, for instance, a fluorescent emission series from one or more samples obtained or captured from a PCR machine, or other source. In step 606, the initial or left-most peak can be identified, for example, the left-most peak labeled indexPeak. In step 608, a first valley to the left of the initially identified indexPeak can be identified, pointed to by a parameter such as indexLeft with height leftHeight. In step 610, a first valley to the right of the initially identified indexPeak can be identified, pointed to by a parameter such as indexRight with height rightHeight. In step 612, a variable pedestalHeight can be set to the maximum of the parameters leftHeight and rightHeight. In step 614, the data segment to the left of indexRight can be thresholded by applying pedestalHeight as a threshold value, thus generating the first peak with the pedestal or low-frequency baseline removed. In step 616, data to the left of indexRight of the current data segment can be recursively removed, to thereby subtract or equalize for the pedestal throughout the source data set. In step 618, processing can end, repeat, return to a prior processing point, or proceed to a further processing point.

According to various embodiments, the dissociation analysis can comprise ranking the detected, pedestal-removed peaks by their relative heights with respect to the tallest peak. According to various embodiments, the user can specify a fractional score as the peak detection threshold, and the analysis can comprise reporting those peaks that have a relative height above that reporting threshold. For example, the tallest peak can be given a fractional score of 100. If a fractional score peak detection threshold is set at 40, then only peaks above 40% of the tallest peak will be reported, and the lower height peaks will be regarded as noise. According to various embodiments, the peaks falling below the peak detection threshold can be removed or discarded. According to various embodiments, the peak detection threshold can be automatically computed, for example based on standard deviation measures on the peaks, or other metrics or measures. According to various embodiments, any of the raw detection data, normalized differential melting curves, or other data, charts, graphs, or information can be stored to, and/or displayed or presented to a user by, a computer, instrument, or other hardware or device.

According to various embodiments, the dissociation or melting curve analysis can take place during, or subsequent to, amplification, or in the absence of amplification. Furthermore, while various embodiments herein are described in connection with PCR, according to various embodiments, other methods of amplification can be compatible with differential dissociation or melting curve analysis according to the present teachings. Moreover, while reference is made to amplification, according to various embodiments, the differential dissociation/melting curve analysis of the present teachings can be performed on nucleic acid samples that have been obtained without amplification, or can be applied to other processes or chemistries. Furthermore, while description is made herein of analyzing DNA or fragments of DNA to determine melting points and other data, according to various embodiments, chemicals, substances, samples, or materials can be analyzed according to the present teachings.

According to various embodiments, different aspects of the differential dissociation/melting curve analysis of the present teachings can be applied to commercial systems and implementations, such as the Step One™ machine commercially available from Applied Biosystems, Foster City, Calif., and described, for example, a publication entitled "Applied Biosystems Step One Real-Time PCR System Getting Started Guide," which publication is incorporated by reference in its entirety herein.

The differential dissociation/melting curve analysis according to various embodiments of the present teachings can be utilized in automated systems and techniques such as those described, for example, in the publication, by Mann et al., entitled "Automated Validation of Polymerase Chain Reactions Using Amplicon Melting Curves," Proceedings of the Computational Systems Bioinformatics Conference, Aug. 8-11, 2005, Stanford, Calif., pp. 377-385, which publication is incorporated by reference in its entirety herein.

Various embodiments of the present teachings can be implemented, in whole or part, in digital electronic circuitry, or in computer hardware, firmware, software, or in combinations thereof. Apparatus of the invention can be implemented in a computer program, software, code, or algorithm embodied in machine-readable media, such as electronic memory, CD-ROM or DVD discs, hard drives, or other storage device or media, for execution by a programmable processor. Various method steps according to the present teachings can be performed by a programmable processor executing a program of instructions to perform functions and processes according to the present teachings, by operating on input data and generating output. The present teachings can, for example, be implemented in one or more computer programs that are executable on a programmable system including at least one programmable processor coupled to receive data and instructions from, and to transmit data and instructions to, a data storage system or memory, at least one input device such as a keyboard and mouse, and at least one output device, such as, for example, a display or printer. Each computer program, algorithm, software, or code can be implemented in a high-level procedural or object-oriented programming language, or in assembly, machine, or other low-level language if desired. According to various embodiments, the code or language can be a compiled, interpreted, or otherwise processed for execution.

Various processes, methods, techniques, and algorithms can be executed on processors that can include, by way of example, both general and special purpose microprocessors, such as, for example, general-purpose microprocessors such as those manufactured by Intel Corp. or AMD Inc., digital signal processors, programmable controllers, or other processors or devices. According to various embodiments, generally a processor will receive instructions and data from a read-only memory and/or a random access memory. According to various embodiments, a computer implementing one or more aspects of the present teachings can generally include one or more mass storage devices for storing data files, such as magnetic disks, such as internal hard disks and removable disks, magneto-optical disks, and CD-ROM DVD, Blu-Ray, or other optical disks or media. Memory or storage devices suitable for storing, encoding, or embodying computer program instructions or software and data can include, for instance, all forms of volatile and non-volatile memory, including for example semiconductor memory devices, such as random access memory, electronically programmable memory (EPROM), electronically erasable programmable memory, EEPROM, and flash memory devices, as well as magnetic disks such as internal hard disks and removable disks, magneto-optical disks, and optical disks. Any of the foregoing can be supplemented by, or incorporated in, ASICs. According to various embodiments, processors, workstations, personal computers, storage arrays, servers, and other computer, information, or communication resources used to implement features of the present teachings can be networked or network-accessible.

Other embodiments will be apparent to those skilled in the art from consideration of the present specification and practice of the present teachings disclosed herein. For example, resources described in various embodiments as singular can, in embodiments, be implemented as multiple or distributed, and resources described in various embodiments as distributed can be combined. It is intended that the present specification and examples be considered as exemplary only.

What is claimed is:

1. A method for biological substance analysis, the method comprising:
    physically dissociating at least one sample of the biological substance by progressively changing a temperature of the at least one sample;
    operating an emission detector to measure intensities of light emitted from a dye bound to the at least one sample as the temperature is progressively changed, thus producing measured intensities of light, wherein the dye remains bound to the at least one sample until the at least one sample is dissociated;
    executing machine instructions by a system processor to cause the system to:
    interpolate the measured intensities of light into a set of interpolated intensities for a plurality of temperatures at equally-spaced temperature intervals of the at least one sample including providing a user interface on a machine display to display a plurality of data points comprising the measured intensities of light at corresponding temperatures, the user interface also providing for marking of data points within a user-specified neighborhood or region, around or in proximity to a particular temperature of the plurality of temperatures and the machine instructions further causing the system to apply a weighting function to the marked data points to generate a new data sample value to be included in the set of interpolated intensities;
    generate a differential dissociation curve from a derivative of the interpolated intensities;
    determine a pedestal using one or more valleys proximate to a particular peak identified in the differential dissociation curve;
    generate an adjusted differential dissociation curve by subtracting the pedestal from one or more peaks of the differential dissociation curve; and
    generate the adjusted differential dissociation curve on a machine display.

2. The method of claim 1, further comprising detecting at least one peak in the differential dissociation curve.

3. The method of claim 1, further comprising modifying the differential dissociation curve.

4. The method of claim 1, further comprising generating a power spectrum of the set of interpolated intensities.

5. The method of claim 1, wherein the derivative comprises a first-order derivative.

6. The method of claim 1, further comprising performing a frequency-domain transform on the set of interpolated intensities.

7. The method of claim 1, wherein the at least one sample comprises a plurality of samples each having associated emission measurements.

8. A system for generating a visualization of a differential dissociation curve of at least one sample on a machine display, comprising:
    an input unit for receiving, from sensors, emission measurements from at least one sample, the sample comprising a dye that remains bound to the sample until the sample is dissociated; and a processor, communicating with the input unit, the processor being configured to cause the system to:
receive the emission measurements from the input unit and record the emission measurements at uneven temperature intervals of the sample;
interpolate the emission measurements into a set of interpolated intensities for a plurality of temperatures at equally-spaced temperature intervals of the at least one sample including providing a on a machine display to display a plurality of data points comprising the emission measurements at corresponding temperatures, the user interface also providing for marking of data points within a user-specified neighborhood or region, around or in proximity to a particular temperature of the plurality of temperatures and the machine instructions further causing the system to apply a weighting function to the marked data points to generate a new data sample value to be included in the set of interpolated intensities;
form a differential dissociation curve from a derivative of the set of interpolated intensities;
determine a pedestal using one or more valleys proximate to a particular peak identified in the differential dissociation curve;
generate an adjusted differential dissociation curve by subtracting the pedestal from one or more peaks of the differential dissociation curve; and
form the adjusted differential dissociation curve on the machine display.

9. The system of claim 8, wherein the processor is further configured to cause the system to:
detect at least one peak in the differential dissociation curve.

10. The system of claim 8, wherein the processor is further configured to cause the system to:
modify the differential dissociation curve.

11. The system of claim 10, wherein modifying the differential dissociation curve comprises removing emission measurements associated with peaks that fall below a peak detection threshold.

12. A computer-readable medium, the computer-readable medium comprising instructions for a computer-implemented method for generating a differential dissociation curve of at least one sample on a machine display, the method comprising:
interfacing with sensors to measure emission intensities of a dye bound to at least one sample, the emission intensities measured at uneven temperature intervals to produce emission measurements, wherein the dye remains bound to the at least one sample until the at least one sample is dissociated and wherein the at least one sample is dissociated by changing the temperature of the at least one sample;
interpolate the emission measurements of the at least one sample into a set of interpolated intensities for a plurality of temperatures at equally-spaced temperature intervals of the at least one sample including providing a user interface on a machine display to display a plurality of data points comprising the emission measurements at corresponding temperatures, the user interface also providing for marking of data points within a user-specified neighborhood or region, around or in proximity to a particular temperature of the plurality of temperatures and the machine instructions further causing the processor to apply a weighting function to the marked data points to generate a new data sample value to be included in the set of interpolated intensities;
generating a differential dissociation curve from a derivative of the interpolated intensities;
determining a pedestal using one or more valleys proximate to a particular peak identified in the differential dissociation curve;
generating an adjusted differential dissociation curve by subtracting the pedestal from one or more peaks of the differential dissociation curve; and
generating the adjusted differential dissociation curve on the machine display.

13. The computer-readable medium of claim 12, wherein the method further comprises:
modifying the differential dissociation curve.

14. The computer-readable medium of claim 12, wherein the method further comprises:
generating a power spectrum of the interpolated emission measurements.

15. The computer-readable medium of claim 12, wherein the derivative of the emission measurements comprises a first-order derivative of the emission measurements.

16. The computer-readable medium of claim 12, wherein the method further comprises performing a frequency-domain transform on the interpolated emission measurements.

17. The computer-readable medium of claim 12, wherein the differential dissociation curve is generated in connection with a polymerase chain reaction process.

* * * * *